United States Patent [19]
Barrett et al.

[11] Patent Number: 5,391,201
[45] Date of Patent: Feb. 21, 1995

[54] METHOD OF USING A CORNEAL RING INLAY

[75] Inventors: Graham D. Barrett, Perth, Australia; Cary J. Reich, Laguna Hills, Calif.

[73] Assignee: Chiron IntraOptics, Inc., Irvine, Calif.

[21] Appl. No.: 267,755

[22] Filed: Jul. 5, 1994

Related U.S. Application Data

[63] Continuation of Ser. No. 993,657, Dec. 21, 1992, abandoned, which is a continuation-in-part of Ser. No. 816,007, Jan. 2, 1992, abandoned.

[51] Int. Cl.$^6$ ............................................. A61F 2/14
[52] U.S. Cl. .................................... 623/5; 128/898
[58] Field of Search ................................. 623/4-6; 606/107; 128/898

[56] References Cited

U.S. PATENT DOCUMENTS

| | | | |
|---|---|---|---|
| 4,781,187 | 11/1988 | Herrick | 623/5 |
| 4,976,732 | 12/1990 | Vorosmarthy | 623/6 |
| 5,123,921 | 6/1992 | Werblin et al. | 623/5 |

FOREIGN PATENT DOCUMENTS 388746 10/1973 U.S.S.R. .................................. 623/5

OTHER PUBLICATIONS

Simon, G., et al. Meeting of the Assoc. for Research in Vision and Ophthalmology, Apr. 30–May 5, 1989, Sarasota, Fla., Poster Abs. 43.

Krasnov, M. M., et al. *Ann. Ophthalmol.*, 24:165-8 (1992).

*Primary Examiner*—Randy C. Shay
*Attorney, Agent, or Firm*—Rothwell, Figg, Ernst & Kurz

[57] ABSTRACT

A biocompatible corneal inlay ring apparatus for altering the curvature of the central optic zone of the cornea of the eye without intrusion into this optic zone, comprising a continuous ring of a fixed diameter greater than that of the optic zone, of a thickness and geometry such that the curvature of the central optic zone is flattened to an extent appropriate to the refractive correction desired, and of a composition having a refractive index within about 2.0% of that of the corneal tissue.

8 Claims, 2 Drawing Sheets

METHOD OF USING A CORNEAL RING INLAY

This is a continuation of application Ser. No. 07/993,657, filed Dec. 21, 1992, now abandoned, which is a continuation-in-part of U.S. patent application Ser. No. 07/816,007, filed Jan. 2, 1992, now abandoned.

BACKGROUND OF THE INVENTION

1. Field of the Invention

The field of this invention relates to corneal implants to correct refractive errors in a patient. More particularly, it relates to a corneal ring inlay device for reversibly altering the curvature of the central cornea without intruding on the central cornea, which is particularly useful in correcting vision defects.

2. Description of the Background Art

Deviations from the normal shape of the corneal surface or the axial length of the eye produce errors of refraction in the visual process. The eye in a state of rest, without accommodation, focuses the image of distant objects exactly on the retina. Myopia is that refractive condition in which, with accommodation completely relaxed, parallel rays are brought to focus in front of the retina. One condition which commonly causes myopia is when the length of the eye is greater than normal. In this condition, rays converge or focus in front of the retina in the vitreous of the eye. When the rays reach the retina, they have diverged, forming a circle of diffusion and consequently a blurred image. A concave lens is needed to correct the focus of the eye for myopia.

The classical treatment of these forms of refractive error of the eye is with the use of eyeglasses or contact lenses, both of which have well-known disadvantages to the user. Recently, surgical keratorefractive techniques have been developed to change the refractive condition of the eye in order to correct both hyperopic and myopic errors. The results of such surgical procedures are not entirely satisfactory. One such technique, referred to as keratomileusis, was introduced by Barraquer of Columbia in 1961. This technique involves grinding of a corneal button into an appropriate shape to correct myopia or hyperopia. It is often unsatisfactory, in part because it often induces additional refractive errors to the eye. These refractive errors are not compensatible, in part because suturing can cause radial asymmetry of the cornea that subsequently results in astigmatic error, and in part because suturing causes scarring of the corneal tissue, which generates scar tissue that is not transparent to light.

In a related surgical technique, keratophakia, a donor cornea is ground into a convex lens and inserted in the lamella in order to correct aphakic hypermetropia. Radial keratotomy was introduced in modern times (1972) by Fyodorov of the USSR to correct astigmatism and myopia. Correction of astigmatism by asymmetrically altering the corneal curvatures is prone to producing aberrant refractive corrections, in part because of suturing and in part because of remodeling of the altered stroma. Such surgery does not have a fully predictable outcome, and furthermore any non-spherical flattening of the cornea on healing results in an eyesight defect that cannot be corrected by lenses.

It is thus seen that present procedures in keratorefractive surgery are best limited to conditions where other more standard corrective practices are found ineffective. It is generally recognized that the limiting factor in such surgical techniques is the complexity involved, not only with multiple incisions in corneal tissue necessary for accomplishing such procedures, but also complex suturing patterns, resulting in a gross restructuring of the eye.

It is thus clear that there is an important need for alternate methods of achieving a change in anterior corneal curvature without extensive surgical intervention.

U.S. Pat. Nos. 4,452,235, 4,671,276, 4,766,895 and 4,961,744 to Kera Vision, Inc. disclose attempts to meet this need with a surgical apparatus consisting of a flexible plastic, split end, flat adjusting ring that is inserted into the stroma of the cornea of the eye. A metal dissecting ring, held in a circular shape by a special holder, is connected to one end of the adjusting ring in order to part the stroma and provide a pathway for the adjusting ring as the ring is rotated through the stroma. The ends of the adjusting ring are moved to change the curvature of the cornea to a desired shape in accordance with the desired visual correction, after which the ends of the adjusting ring are hooked to each other in order to maintain the desired shape; the dissecting head is then detached from the adjusting ring and removed from the eye. Due to the resulting stress on the cornea, such rings may erode through the cornea, resulting in severe damage.

In oral presentations at a January 1988 meeting of CLAO and at a May 1989 meeting of ARVO, E. Barraquer described flat, intrastromal rings for correction of myopia consisting of thin sections cut from silicon tubing. Ring were inserted by dissecting a large intrastromal pocket, and then inserting the flexible silicone ring into the pocket. The surface of the cornea was cut only at the point of the initial incision; Bowman's membrane was not cut in a circular fashion.

Zhivotovskii, D. S., USSR patent no. 388746, describes an alloplastic, flat, geometrically regular, annular ring for intracorneal implantation of an inside diameter that does not exceed the diameter of the pupil. Refractive correction is accomplished primarily by making the radius of curvature of the surface of the ring larger than the radius of curvature of the surface of a recipient's cornea in order to achieve flattening of the central area of the cornea. Surgical procedures for inserting the rings are not described.

Krasnov, M. M., *Ann. Ophthalmol.*, 24:165 (1992) describes a machined homoplastic annular transplant to be grafted on top of the cornea concentrically with the visual axis in order to correct myopia.

The advantages of a ring system for altering the curvature of the cornea, but one without the complicated apparatus and surgical and erosion problems attendant upon the use of the aforementioned split end apparatus, are encompassed in the present invention which is disclosed and claimed below.

SUMMARY OF THE INVENTION

The present invention provides a corneal continuous ring inlay that alters the curvature of the central cornea to correct for refractive error in a facile and simple manner by placing inside the stroma a continuous corneal ring of a fixed diameter, and of a thickness and geometry that alters the curvature of the central portion, i.e., optical zone, of the cornea, without encroaching on this central portion and without impeding the flow of nutrients to the anterior cornea.

It is thus an aspect of this invention to describe cosmetically acceptable corneal ring implants that produce changes in corneal curvature.

It is yet another object of this invention to disclose methods of use of the ring inlay using surgical procedures for inserting the ring that do not result in extrusion of the ring, and that are reversible.

These and other objects will become apparent by reference to the specification that follows and to the appended claims.

DETAILED DESCRIPTION OF THE FIGURES

DETAILED DESCRIPTION OF THE INVENTION

The invention relates to a biocompatible ring-shaped device that alters the curvature of the central cornea of the eye without intrusion into the optic zone of the cornea. The ring comprises a continuous corneal ring of fixed diameter insertable into the stroma of the cornea. The inside diameter of the ring is greater than the optic zone so that the ring does not overlay the optic zone. The ring's cross-sectional thickness and geometry are such that the anterior cornea is raised peripherally, thereby reducing the curvature of the cornea in its central portion, i.e., the optic zone, thereby producing the optical correction desired.

Figure 1B:
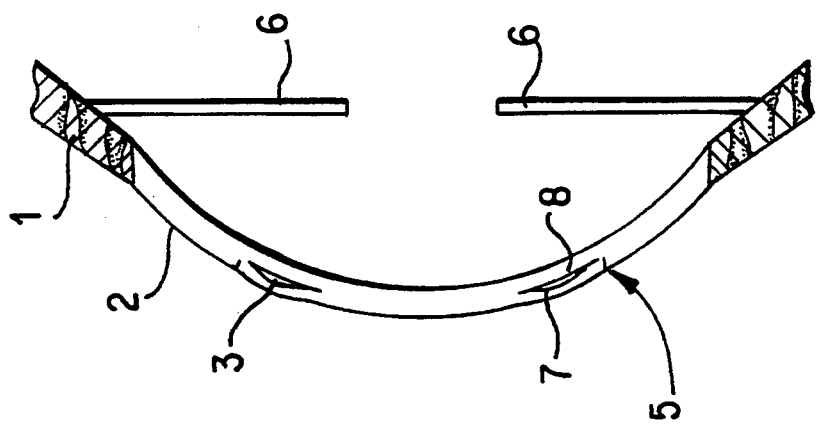
FIG. 1 is a front (A) and side (B) view of the general location of the corneal ring inlay of the invention in the cornea of the eye. The inner diameter of the ring is such that the ring avoids intrusion into the optic zone of the cornea.
Figure 1A:
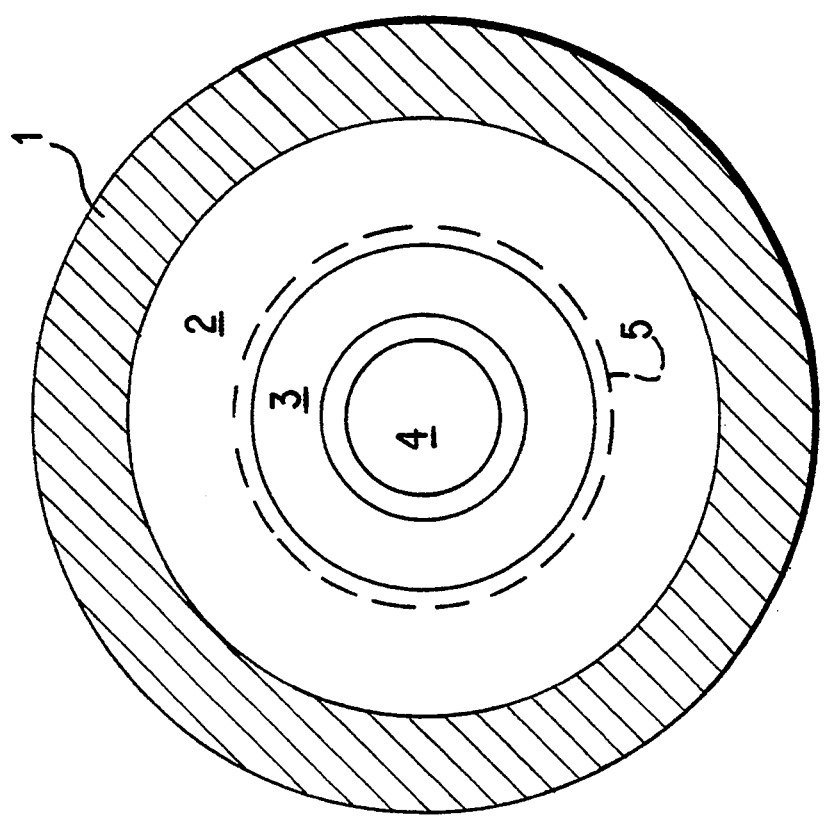

Referring to FIG. 1 A (front view) and B (side view), which show one embodiment of the invention, the ring inlay 3 is inserted in the cornea 2 via a surgical incision in the stroma 5 peripheral to the optic zone 4 and over the iris 6. Both the cornea 2 and iris 6 are attached to the sclera 1 of the eye.

In a preferred embodiment, the anterior surface 7 of the corneal ring 3 is of a substantially domed shape and the posterior surface 8 is substantially flat, with the ring being thickest in the middle of the dome and thinnest at the inner and outer extremes of the ring.

Figure 2:
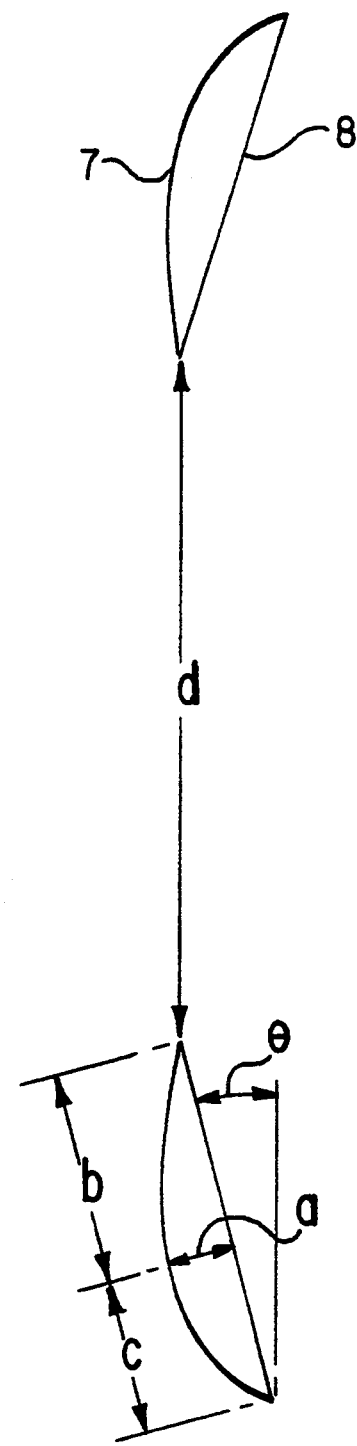
FIG. 2 is a cross-sectional view of a corneal ring inlay for insertion within the stromal tissue of the cornea of the eye. The cross-sectional shape of the corneal ring inlay has a thickness and geometry that alters the curvature of the optic zone of the cornea.

The geometry of corneal inlay ring 3 is shown in greater detail in FIG. 2. The extent of corneal flattening and thus refractive correction is determined by a number of factors. These factors include the cross-sectional thickness a and inner and outer slopes of the dome-shaped anterior surface 7, which are determined by the ratio of thickness dimension a to dimensions b and c, respectively. For a given shape of ring cross-section, the inside ring diameter d also affects the extent of refraction correction. Refractive correction by the corneal inlay ring of the invention is not a function of the differences in radii of curvature of the corneal surface in relation to that of the anterior surface of the ring. As illustrated in the drawings, when implanted, the posterior surface 8 of corneal ring inlay 3 has a frustoconical shape so as to conform generally to the curvature of the cornea for comfortable fit. When the corneal ring inlay is made of a highly flexible material, the ring may be molded or machined so that the posterior aspect is substantially flat, and it will, when implanted, assume the frustoconical shape. When the corneal ring inlay is made of a more rigid material, it is advantageously molded or machined into the requisite frustoconical shape. When the corneal ring inlay is made of a relatively rigid material, the angle $\theta$ is selected so that posterior surface 8 conforms generally to the curvature of the cornea. Typical values for dimension a range from about 0.005 to about 0.2 mm. Typical values for dimensions b and c range from about 0.1 to about 2 mm. Typical values for angle $\theta$ range from about 0 to about 45 degrees. Typical values for diameter d range from about 2 to about 8 mm.

Referring to FIG. 1, in one embodiment the surgical procedure requires a peripheral incision 5 in the cornea 2 through Bowman's membrane, followed by undermining the stroma in a circular fashion, leaving intact the central portion of the cornea. The cutting of Bowman's membrane throughout results in little stress on the cornea after placing the ring into the undermined portion of the stroma. The initial peripheral circular incision may be at a site in the limbus. In another embodiment, the circular trephine incision through Bowman's membrane is made at a point outside of the optical zone, and the stroma of the cornea is undermined from the inside out toward the limbus. Thereafter, the periphery of the tissue may be resealed by suturing, adhesive or laser tissue sealing, or by allowing the circular incision to reseal naturally. The central portion of the cornea, i.e., the optic zone 4, is left entirely intact subsequent to the procedure, as the ring device is located peripherally to the central optic zone, i.e., over the iris 6. The procedure is readily and simply reversible, allowing facile removal of the ring.

Another embodiment involves slicing off the top of the cornea through the optical zone, placing a ring of the invention, of a diameter such that all of the ring is outside of the optical zone, onto the resulting stromal bed, and replacing the cap of the cornea. As in the first two embodiments, the cap may be reconnected to the cornea by suturing, adhesive or laser tissue sealing, or simply by allowing natural sealing to occur. The cap will heal quickly and will leave the optical zone unchanged. The net effect of this embodiment, as with the first two, is to correct vision by central anterior flattening of the cornea which is due to the anterior peripheral bulge caused by the ring.

Advantageously, the corneal ring inlay of the invention does not impede permeation of nutrients and gases. The refractive index of the ring itself is not a factor because of its location peripheral to the optic zone; therefore, a high water content (e.g., 72%) biocompatible, permeable hydrogel ring may be advantageously used in accordance with this invention. Alternatively, flexible materials such as silicone or urethanes, or hard plastics such as polysulfone or PMMA, may also be used. The refractive index of the inlay ring should be within 2% of the refractive index of the corneal tissue which is adjacent to the ring. It is preferred to use ring inlays of refractive index between 1.350 and 1.400, most preferably between 1.370 and 1.386. As the refractive index of corneal tissue is about 1.376, rings of the preferred indices will not scatter light nor be visible, which is cosmetically desirable.

Important advantages of the use of the above-described corneal ring inlays include: (a) reversibility of the procedure, that is to say, removal of the inlay, should this be desired, and (b) alteration of the central cornea's curvature without placing any stress upon it.

This latter advantage assures complete freedom from the potential for corneal scarring that could cause optical aberrations.

The following examples are merely exemplary of the use of the ring apparatus of the invention and are not to be construed as in any way limiting the scope of the invention which is disclosed in the specification and appended claims.

EXAMPLE 1

Insertion of Inlay Ring in Human Eyes in Vitro

High water content hydrogel rings were implanted in the corneas of five human eyes from cadavers. While all rings had an outside diameter of 7 mm, the inside diameters of individual rings (d in FIG. 2) were either 3 mm or 4 mm.

Rings were implanted using the following surgical technique. An 8.0 to 8.5 mm diameter Hessburg-Barron trephine was used to make a circular keratomy approximately 0.2 to 0.3 mm deep in the stroma. The wound was then undermined towards the optic zone to a diameter equal to the inner diameter (3 mm or 4 mm) of the ring to be implanted. The ring was then inserted using the "tire-iron" approach. The resulting wound was sutured using either interrupted or running suture techniques.

The corneal topography of each eye was examined using corneoscopy and the Eye-Sys corneal topography system. Comparison of pre-surgery with post-surgery corneas revealed flattening of the corneas in eyes in which the ring of the invention had been implanted. Rings of different thicknesses produced different degrees of flattening.

EXAMPLE 2

Insertion of Inlay Ring In Pig Eyes in Vitro

The rings and procedure of Example 1 were used with pig eyes. Corneal topography comparisons revealed the same type of corneal curvature flattening by the rings as in Example 1.

EXAMPLE 3

Insertion of Inlay Ring in Rabbit Eyes in Vivo

High water content hydrogel rings were implanted in rabbit eyes in vivo and observed over a period of two months using the same rings and procedure as in Example 1. Typically, sutures were removed between weeks two and three post-operatively. All eyes exhibited flattening of the cornea as determined by visual observation. Examination of a rabbit eye eight months post-surgery revealed a clear and healthy cornea with an equally clear ring implant.

EXAMPLE 4

Inserting of Inlay Ring in Rabbit Eyes in Vivo

A ring was punched from a 72% water content contact lens, such that the internal diameter was approximately 6.5 mm and the outside diameter was approximately 8 mm. The thickness of the ring was approximately 0.1 mm.

For implantation of the ring, a 6.0 mm diameter Hessburg-Barron trephine was used to make a circular cut approximately 0.2 mm deep into the stroma. The wound was then undermined away from the optic zone (towards the periphery) to a diameter equal to about 8.5 mm. The ring was inserted using the "tire-iron" approach. The resulting wound was allowed to reseal naturally without sutures.

Examination of the rabbit four day after surgery revealed some corneal flattening.

I claim:

1. A method for altering the curvature of the central optical region of the cornea of the eye of a patient, comprising:
    a) making a circular peripheral cut in the cornea peripheral to the optical zone;
    b) undermining the stroma through Bowman's membrane in a circular fashion;
    c) placing into the undermined portion of the stroma an inlay ring apparatus composed of a biocompatible continuous ring of a material having a geometry effective for altering the curvature of the cornea; and
    d) resealing the periphery of the tissue.

2. A method according to claim 1 wherein Bowman's membrane is undermined in a circular fashion toward the limbus of the eye.

3. A method according to claim 2 further comprising, prior to step c), providing an inlay ring apparatus that is composed of a material having refractive index within about 2% of the refractive index of adjacent corneal tissue.

4. A method according to claim 1 wherein Bowman's membrane is undermined in a circular fashion toward the optic zone of the eye, leaving the optic zone intact.

5. A method according to claim 4 further comprising, prior to step c), providing an inlay ring apparatus that is composed of a material having refractive index within about 2% of the refractive index of adjacent corneal tissue.

6. A method according to claim 1 further comprising, prior to step c), providing an inlay ring apparatus that is composed of a material having refractive index within about 2% of the refractive index of adjacent corneal tissue.

7. A method according to claim 1 wherein the resealing step comprises resealing the periphery of the tissue either naturally, with sutures, with an adhesive or with a laser beam.

8. A method according to claim 1 further comprising, prior to step c), providing an inlay ring apparatus that has a fixed diameter.

* * * * *